(12) United States Patent
Morse et al.

(10) Patent No.: US 8,328,901 B2
(45) Date of Patent: Dec. 11, 2012

(54) INTEGRATED CONTAINMENT SYSTEM

(75) Inventors: Thomas C. Morse, Greenville, NC (US); Mark Huza, Columbia, MD (US)

(73) Assignee: Camfil Farr, Inc., Riverdale, NJ (US)

( * ) Notice: Subject to any disclaimer, the term of this patent is extended or adjusted under 35 U.S.C. 154(b) by 0 days.

(21) Appl. No.: 13/525,990

(22) Filed: Jun. 18, 2012

(65) Prior Publication Data

US 2012/0246910 A1    Oct. 4, 2012

Related U.S. Application Data

(63) Continuation of application No. 13/236,440, filed on Sep. 19, 2011, now Pat. No. 8,202,337, which is a continuation of application No. 13/007,843, filed on Jan. 17, 2011, now Pat. No. 8,048,182, which is a continuation of application No. 12/819,732, filed on Jun. 21, 2010, now Pat. No. 7,896,938, which is a continuation of application No. 11/380,737, filed on Apr. 28, 2006, now Pat. No. 7,758,664.

(60) Provisional application No. 60/706,516, filed on Aug. 9, 2005.

(51) Int. Cl.
   *B01D 46/00* (2006.01)
(52) U.S. Cl. ............ 95/1; 55/481; 55/506; 95/273; 96/417
(58) Field of Classification Search ............ 95/273; 96/414; 210/85, 435, 450, 451, 764; 55/385.2, 55/405, 420, 505, DIG. 31; 52/506.05, 506.08; 454/187
See application file for complete search history.

(56) References Cited

U.S. PATENT DOCUMENTS

| | | | | | |
|---|---|---|---|---|---|
| 3,828,527 | A | * | 8/1974 | Briggs et al. | 96/4 |
| 4,193,844 | A | * | 3/1980 | Neumann et al. | 55/309 |
| 4,457,336 | A | * | 7/1984 | Allan et al. | 137/601.04 |
| 4,494,403 | A | * | 1/1985 | Bowers et al. | 73/40.7 |
| 4,521,234 | A | * | 6/1985 | Peebles et al. | 55/481 |
| 4,548,068 | A | * | 10/1985 | Gualtieri et al. | 73/40.7 |
| 5,192,343 | A | * | 3/1993 | Henry | 96/402 |
| 5,244,480 | A | * | 9/1993 | Henry | 96/402 |
| 5,256,375 | A | * | 10/1993 | Morris | 422/500 |
| 5,803,954 | A | * | 9/1998 | Gunter et al. | 95/268 |
| 6,149,699 | A | * | 11/2000 | Grantham | 55/385.2 |
| 2003/0192822 | A1 | | 10/2003 | Cherry | |
| 2006/0243132 | A1* | | 11/2006 | Morse | 95/23 |

FOREIGN PATENT DOCUMENTS

| | | |
|---|---|---|
| EP | 0046740 A2 | 3/1982 |
| JP | 63-252521 A | 10/1988 |
| JP | 63-264116 A | 11/1988 |
| JP | 3015653 U | 6/1995 |
| JP | 10-206310 A | 8/1998 |
| JP | 2002-243626 A | 8/2002 |
| JP | 2003-344308 A | 12/2003 |

\* cited by examiner

*Primary Examiner* — Duane Smith
*Assistant Examiner* — Christopher P Jones
(74) *Attorney, Agent, or Firm* — Patterson & Sheridan, LLP

(57) ABSTRACT

Embodiments of the invention generally provide a containment system having integrated bubble tight-dampers. In another embodiment, the containment system includes an integral auto-scan mechanism disposed in the housing of the containment system so that a filter element, disposed in the housing, may be leak tested without accessing the interior of the housing. In yet another embodiment, a method for testing a filter disposed in a containment system includes challenging an upstream side of a filter element disposed in a housing of the containment system with a test aerosol, and automatically moving a probe disposed within the housing to obtain samples for leak testing.

11 Claims, 7 Drawing Sheets

INTEGRATED CONTAINMENT SYSTEM

CROSS-REFERENCE TO RELATED APPLICATIONS

This application is a continuation of U.S. patent application Ser. No. 13/236,440, filed Sep. 19, 2011, now U.S. Pat. No. 8,202,337 B2, which is a continuation of U.S. patent application Ser. No. 13/007,843 filed Jan. 17, 2011, now U.S. Pat. No. 8,048,182 B2, which is a continuation of U.S. patent application Ser. No. 12/819,732 filed Jun. 21, 2010, now U.S. Pat. No. 7,896,938 B2, which is a continuation of U.S. patent application Ser. No. 11/380,737 filed Apr. 28, 2006, now U.S. Pat. No. 7,758,664 B2, which claims benefit from U.S. Provisional Patent Application No. 60/706,516, filed Aug. 9, 2005, all of which are incorporated by reference in their entireties. This application is related to U.S. Pat. No. 7,658,787 B2 issued to Thomas C. Morse entitled "EXHAUST FILTER MODULE WITH MECHANICALLY POSITIONABLE SCAN PROBE", which is also incorporated by reference in its entirety.

BACKGROUND OF THE INVENTION

1. Field of the Invention

The invention generally relates to a containment housing having integrated dampers. The invention also relates to a containment housing having an integrated filter leak scanning mechanism.

2. Description of the Related Art

FIG. 1 depicts a conventional containment system. A conventional containment system typically consists of multiple components arranged in series. The components generally include one or more filter housing sections, an upstream test section, a downstream test section and rotating vane-type bubble-tight dampers for isolating the system from the upstream and downstream ductwork to which the system is coupled.

The bubble-tight dampers are located upstream and downstream of the filter housing and test sections, which allow the containment system to be sealed air-tight during system decontamination and/or filter servicing. Transitions are disposed between the bubble-tight dampers and the testing and other components of the containment system. The dampers may be bolted or welded to the transitions.

The upstream test section is for the introduction of a challenge aerosol upstream of the filter components and for the measurement of upstream challenge concentration. Conventional upstream test sections typically include baffles to achieve adequate aerosol mixing such that testing may be performed to ANSI, IEST or other standard. The filter housing sections may hold one or more prefilters, intermediate filters, HEPA filters, HEGA filters and/or other filtration components required for the specific application. It is contemplated that the filter 104 may be a panel filter, v-bank filter or other type of filter configuration.

The scan test section is used to conduct manual in-place scan testing and validation of the HEPA filter(s) to determine the location and size of any leaks in the filter(s). A bag with gloves (not shown) is generally coupled to a door flange of the scan test section and utilized to position a probe during testing of a filter disposed in the filter housing section.

This configuration for a conventional containment system is very large, typically in the range of about 130 inches in length, and requires significant space and cost for installation. Moreover, the large size of the components, typically fabricated from stainless steel, results in high material costs. Furthermore, each access door, bag ring, and joint between the multiple sections is a potential leak point. As containment systems are relied upon in labs testing the most toxic and virulent chemicals, agents, viruses and organisms, each potential leak point represents a source for a potential catastrophic biohazard release that could expose technicians and/or the surrounding environment.

Thus, there is a need for an improved containment system having smaller foot print and lower fabrication costs, which also improves the system's inherent safeguards against potential leaks.

SUMMARY OF THE INVENTION

Embodiments of the invention generally provide a containment system having integrated bubble tight-dampers. In another embodiment, the containment system includes an integral auto-scan mechanism disposed in the housing of the containment system so that a filter element, disposed in the housing, may be leak tested without accessing the interior of the housing.

In yet another embodiment, a method for testing a filter disposed in a containment system includes challenging an upstream side of a filter element disposed in a housing of the containment system with a test aerosol, and automatically moving a probe disposed within the housing to obtain samples for leak testing.

BRIEF DESCRIPTION OF THE DRAWINGS

The accompanying drawings, which are incorporated in and constitute a part of the specification, schematically illustrate the present invention, and together with the general description given above and the detailed description given below, serve to explain the principles of the invention.

FIG. 5 depicts a section view of the containment system of FIG. 2;

FIG. 7 depicts another embodiment of a containment system; and

To facilitate understanding, identical reference numerals have been used, where possible, to designate identical elements that are common to the figures. It is contemplated that elements of one embodiment may be beneficially incorporated in other embodiments.

DETAILED DESCRIPTION

The present invention includes one or more of the following features:

Filter housing(s) and test sections incorporated into a single housing, thereby eliminating potential leak points such as multiple bolted or welded connections of individual sections.

Damper blade and sealing surface are integrated into a containment housing as opposed to being a separate damper.

Figure 1:
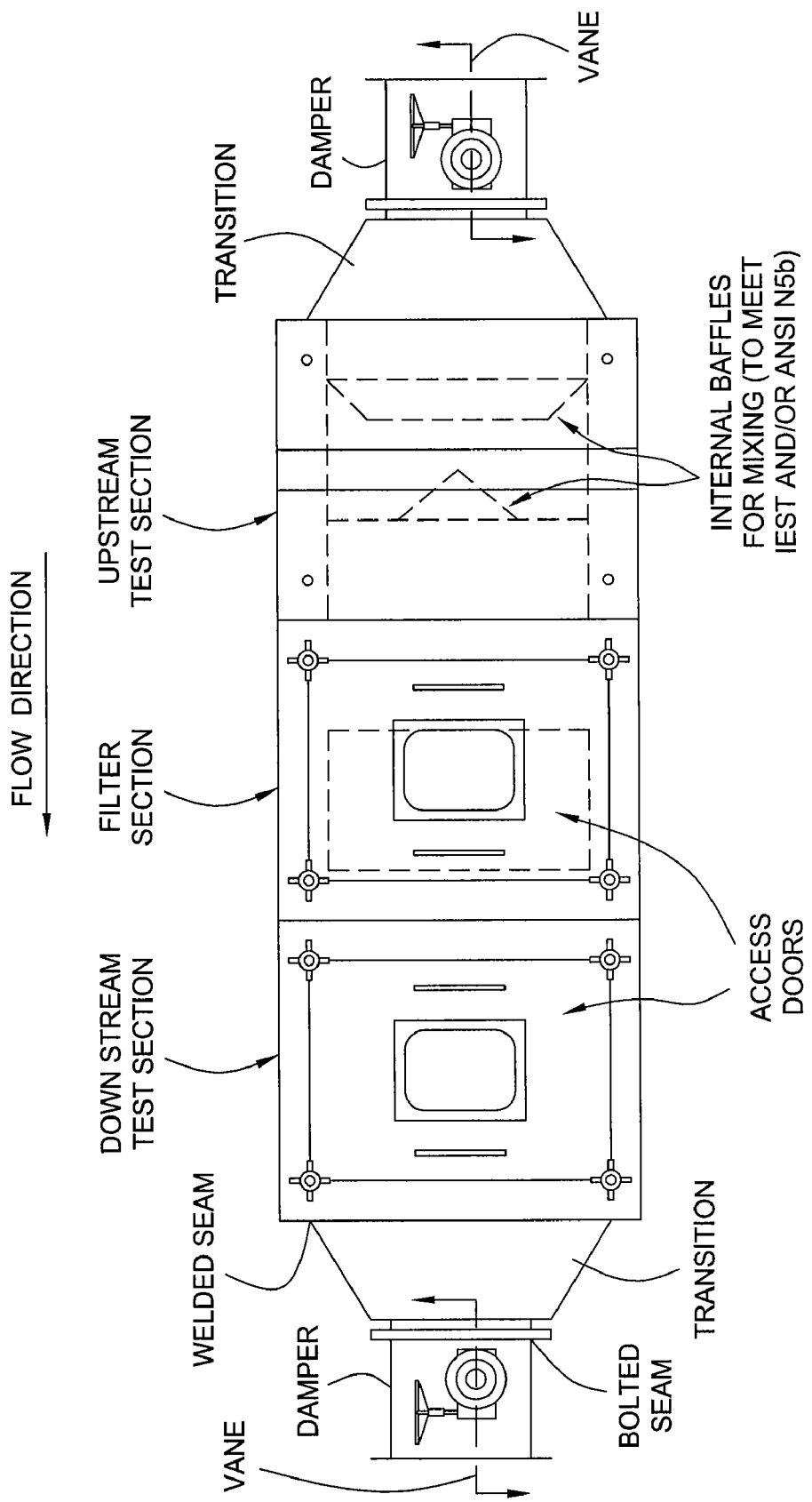
FIG. 1 is a side view of a conventional containment system.

Damper utilizes the body of the containment housing as the external pressure boundary, as opposed to a separate housing such as the barrel of a damper (such as shown in the conventional system depicted in FIG. 1).

The damper "seal plate" or sealing surface and inlet flange are attached directly to the end of the containment housing. They are an integral part of the containment housing.

Beneficially, the integrated damper eliminates potential leak points such as multiple bolted or welded connections (e.g., such as the damper and transition shown in the conventional system depicted in FIG. 1).

The damper blade remains facing in the inlet air stream during operation. Thus, the damper blade also functions as distribution plate to ensure compliance with: IEST-RP-CC034.1 for aerosol uniformity and/or IEST-RP-CC002.2 for airflow uniformity and/or airflow distribution per ASME N510, Section 8, 1995 Reaffirmed and/or air-aerosol mixing uniformity per ASME N510, Section 9, 1995 Reaffirmed. This eliminates the need for internal baffles and space for mixing, thereby allowing the housing to be shortened.

The design and location of the aerosol injection ring is such that aerosol is injected into the high-velocity air coming through the inlet collar of the upstream damper. The location of the aerosol injection ring relative to the damper eliminates the need for distribution plates further downstream of the damper. Whereas, conventional systems utilize separate dampers and aerosol injection housings.

The combination of the aerosol injection ring design and position relative to the damper, the design of the damper, and the location of the damper and aerosol injection ring relative to the inlet of the containment housing comprise an "integrated system" that typically consists of several individual components welded together in series (e.g., a damper, and test section). This integrated system reduces the overall length, installation costs, manufacturing costs, and the installation space requirements as compared to conventional containment systems.

An integrated autoscan mechanism is provided in the housing of the containment system. This allows filters, disposed in the containment system, to be tested without opening and exposing technicians to the downstream interior side of the filter housing.

Figure 2:
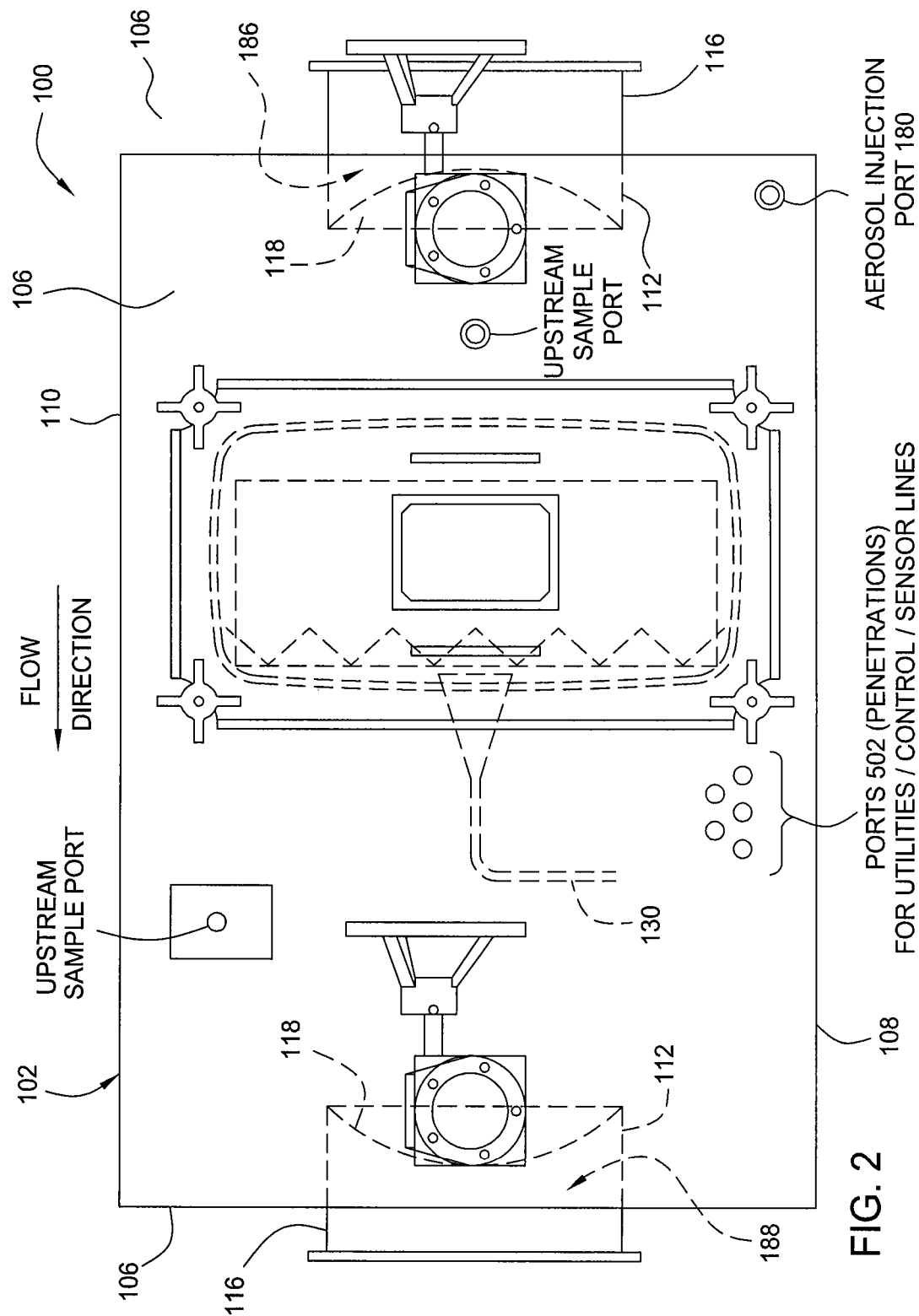
FIG. 2 depicts one embodiment of a containment system having integrated bubble-tight dampers.

FIG. 2 shows a containment system 100 having integrated dampers 118. The containment system 100 generally includes a housing 102 which sealingly holds a filter element or filter 104 therein. In one embodiment, the housing 102 includes a bottom 108, sidewalls 106 (of which the front, left end, and right end sidewalls are shown) and a top 110. The housing 102 may be fabricated from any suitable material such as plastic, fiberglass, stainless steel and aluminum, among other suitable materials. In the embodiment depicted in FIG. 1, the bottom 108, sidewalls 106 and top 110 are continuously welded into a single housing 102 having a substantially rectangular shape.

Figure 3A:
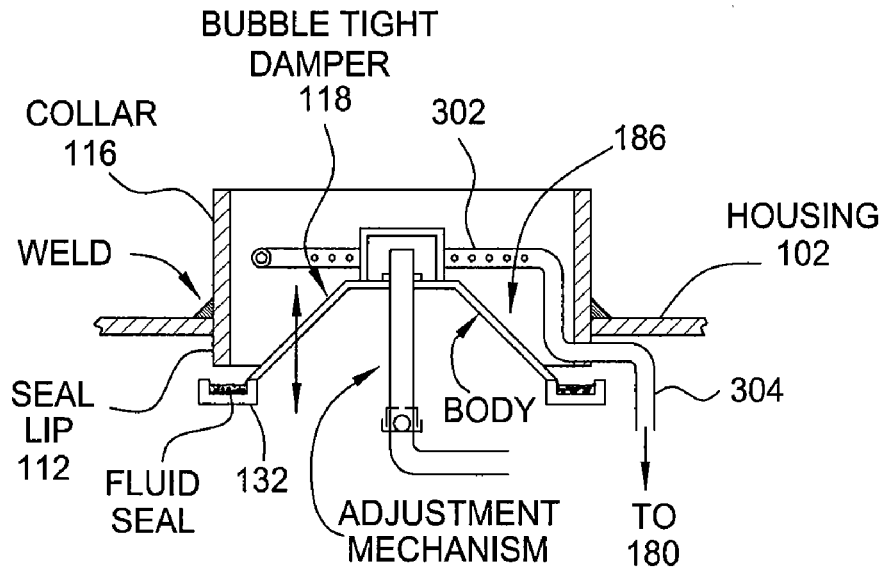
FIG. 3A is a partial sectional view of the containment system of FIG. 2 illustrating one embodiment of a bubble-tight damper.

Referring additionally to the sectional view of FIG. 3A, the housing 102 includes collars 116 disposed around inlet and outlet apertures 186, 188 formed in opposing parallel sidewalls 106. The collars 116 are sealingly coupled to or formed in the sidewalls 106 to facilitate the flow of air (or other fluid) though the filter 104 disposed in the containment system 100. The collars 116 may be sealed to the housing 102 by a continuous weld, caulk, gasket or other suitable seal. The collars 116 include a sealing lip 112 that extends into the interior volume of the housing 102.

A bubble-tight damper 118 is provided in each collar 116. The damper 118 may be moved to between a first position that sealingly engages the lip 112, thereby preventing leakage through the collar 116, and a second position spaced-apart from the lip 112. The distance between the damper 118 and lip 112 may be set to control the rate of flow through the collar 116. In one embodiment, the damper 118 has a generally conical shape that remains in a fixed orientation relative to the damper's open and closing motion, which is axially along the centerline of the collar 116. Thus, as the damper 118 remains facing the flow (e.g., the face of the damper is maintained at a right angle to the flow) through the collar 116, a uniform air gap is maintained between the damper and lip 112 of the collar 116 resulting in uniform air flow distribution through the damper's full range of motion. One damper that may be adapted to benefit from the invention is described in U.S. patent application Ser. No. 10/863,629 filed Jun. 8, 2004, by Morse et al., which is hereby incorporated by reference in its entirety.

In the embodiment depicted in FIG. 3A, the damper 118 includes a gel-filled track 132 formed at the perimeter of a conical body that selectively provides a bubble-tight seal when engaged with the lip 112 extending from the housing 102 and/or collar 116. The phrase "conical body" is intended to include conical, ellipsoidal, hemispherical and round in forms, along with variations thereof. The gel may be a silicon gel, polyurethane gel, or other material suitable for selectively sealing the damper 118 to the containment system 100. Alternatively, a bubble-tight seal may be formed by a gasket or other suitable material. The bubble-tight seal allows an interior volume of the containment system 100 to be isolated from the ducts (not shown) coupled to the collar 116. In this manner, the interior volume of the housing 102 may be decontaminated and/or the filter 104 be replaced. As the damper 118 is integrated directly into the housing 102 without transitions and/or a separate damper module (as shown in the conventional system depicted in FIG. 1), multiple potential leak points are eliminated, increasing the inherent safety factor of the containment system 102 to inadvertent leakage and possible release of contaminants.

Figure 4:
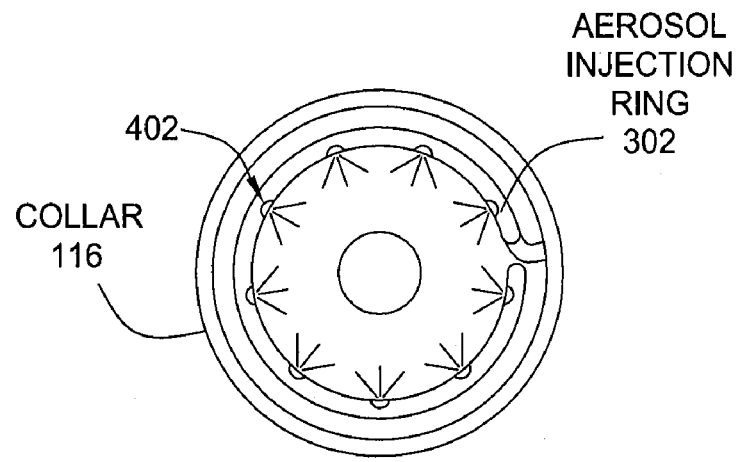
FIG. 4 is a partial top view of the containment system of FIG. 2 illustrating one embodiment of an aerosol injection ring.

Referring additionally to the partial top view of the containment system 100 depicted in FIG. 4, an aerosol injection ring 302 is disposed in the collar 116 upstream of the damper 118. The aerosol injection ring 302 is coupled by a tube 304, sealingly passing through the lip 112, to an aerosol injection port 180 formed through the housing 102. The aerosol injection ring 302 is positioned in the high velocity flow of area defined by the collar 116. Aerosol, provided to the air stream through holes positioned on the radially inward side (or other portion) of the aerosol injection ring 302, impinges on the face of the damper 118 as the air stream enters the housing 102, thereby proving the turbulence necessary to ensure good mixing and uniform distribution of aerosol for filter testing.

Figure 3B:
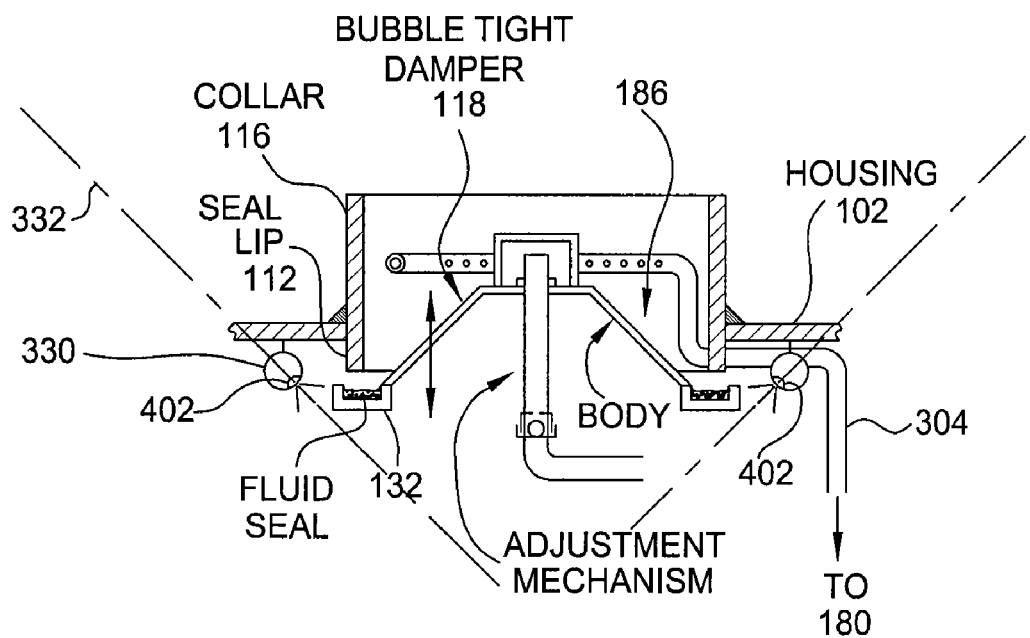
FIG. 3B is a partial sectional view of the containment system of FIG. 2 illustrating an alternative location for an aerosol injection ring.

FIG. 3B is a partial sectional view of the containment system of FIG. 2 illustrating an alternative location for an aerosol injection ring 330. The injection ring 330 is positioned inside the housing 102 and outward from the lip 112. The injection ring 330 is disposed between the sidewall 106 and damper 106. Holes 402 formed in the injection ring 330 have an orientation (shown by dashed line 332) which directs the spray of aerosol into the housing 102 at an inward angle (e.g., toward the centerline of the collar 116) such that the spray is directed into the high velocity air flow zone defined between the lip 112 and damper 118. The orientation 332 may also be away from the sidewall 106 so that the spray exiting the holes 402 clears the lip 112.

These configurations of the aerosol injection ring 330 as shown in FIGS. 3A-B have demonstrated compliance with, IEST-RP-CC034.1 for aerosol uniformity, and/or IEST-RP-CC002.2, for airflow uniformity and/or airflow distribution per ASME N510, Section 8, 1995 Reaffirmed, and/or air-aerosol mixing uniformity per ASME N510, Section 9, 1995 Reaffirmed. Thus, the need for internal baffles and space for mixing required in conventional contamination systems is eliminated, thereby allowing the housing to be shortened, as compared to conventional containment systems.

Figure 6:
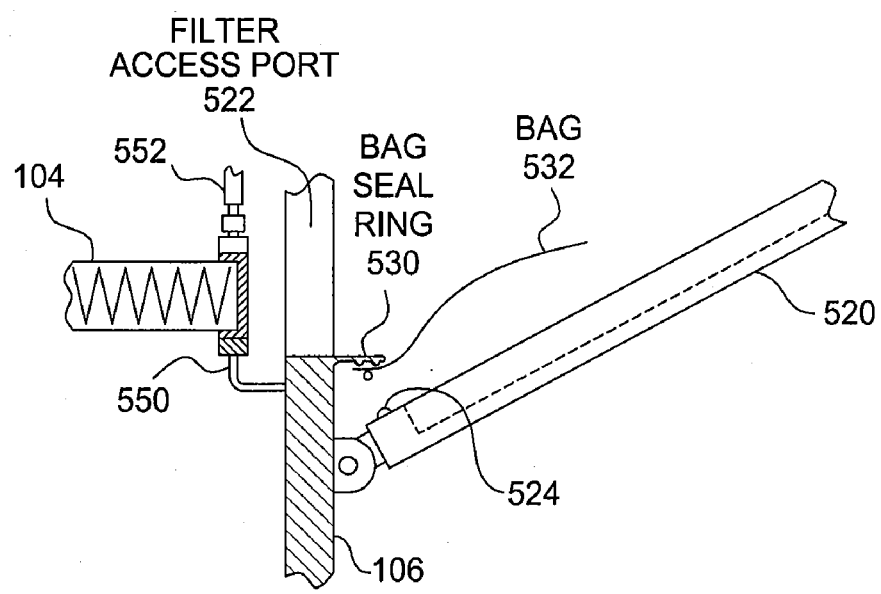
FIG. 6 depicts a partial section view of a bag ring coupled to the housing of the containment system of FIG. 2.
Figure 5:
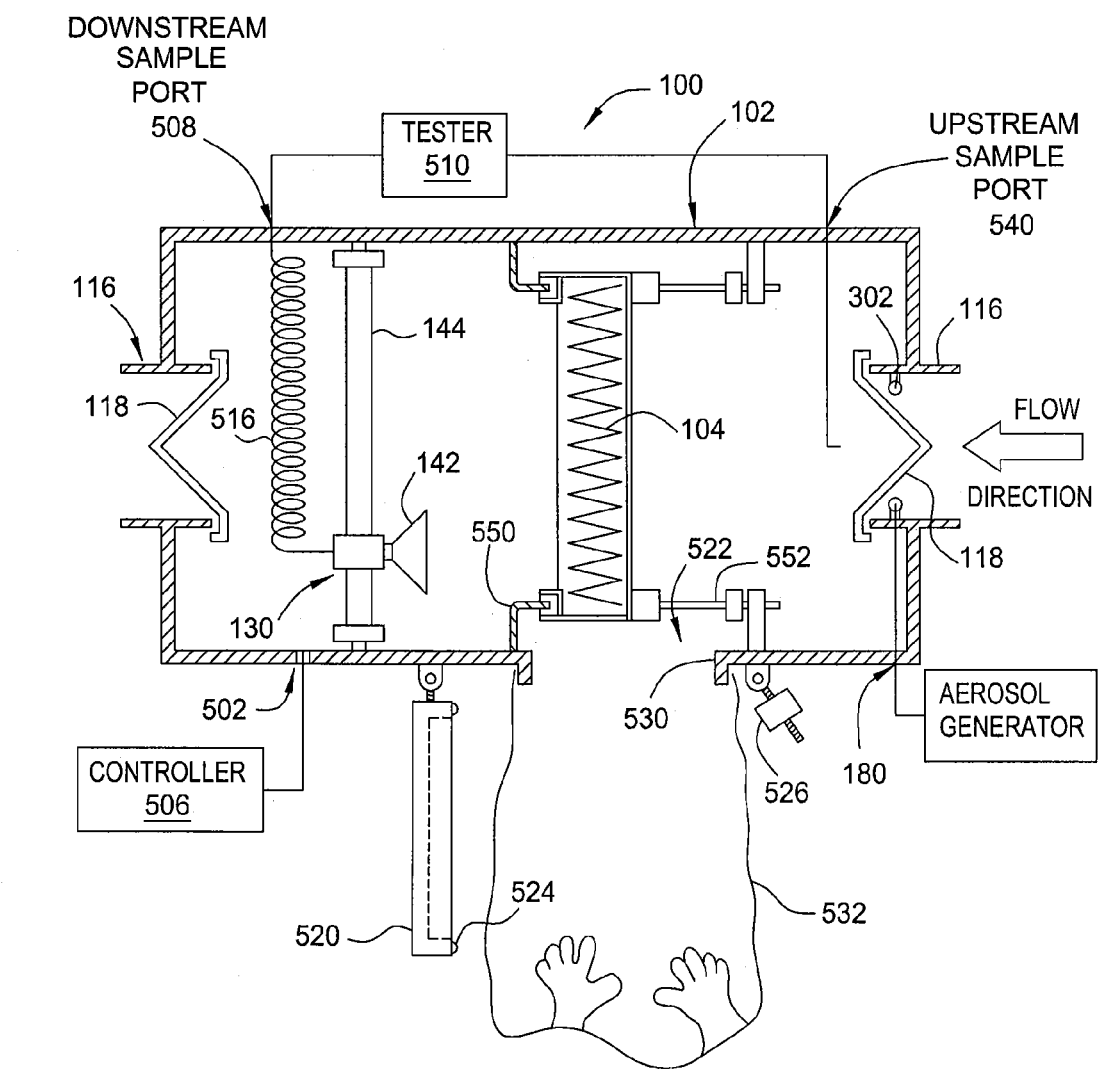
Figure 8:
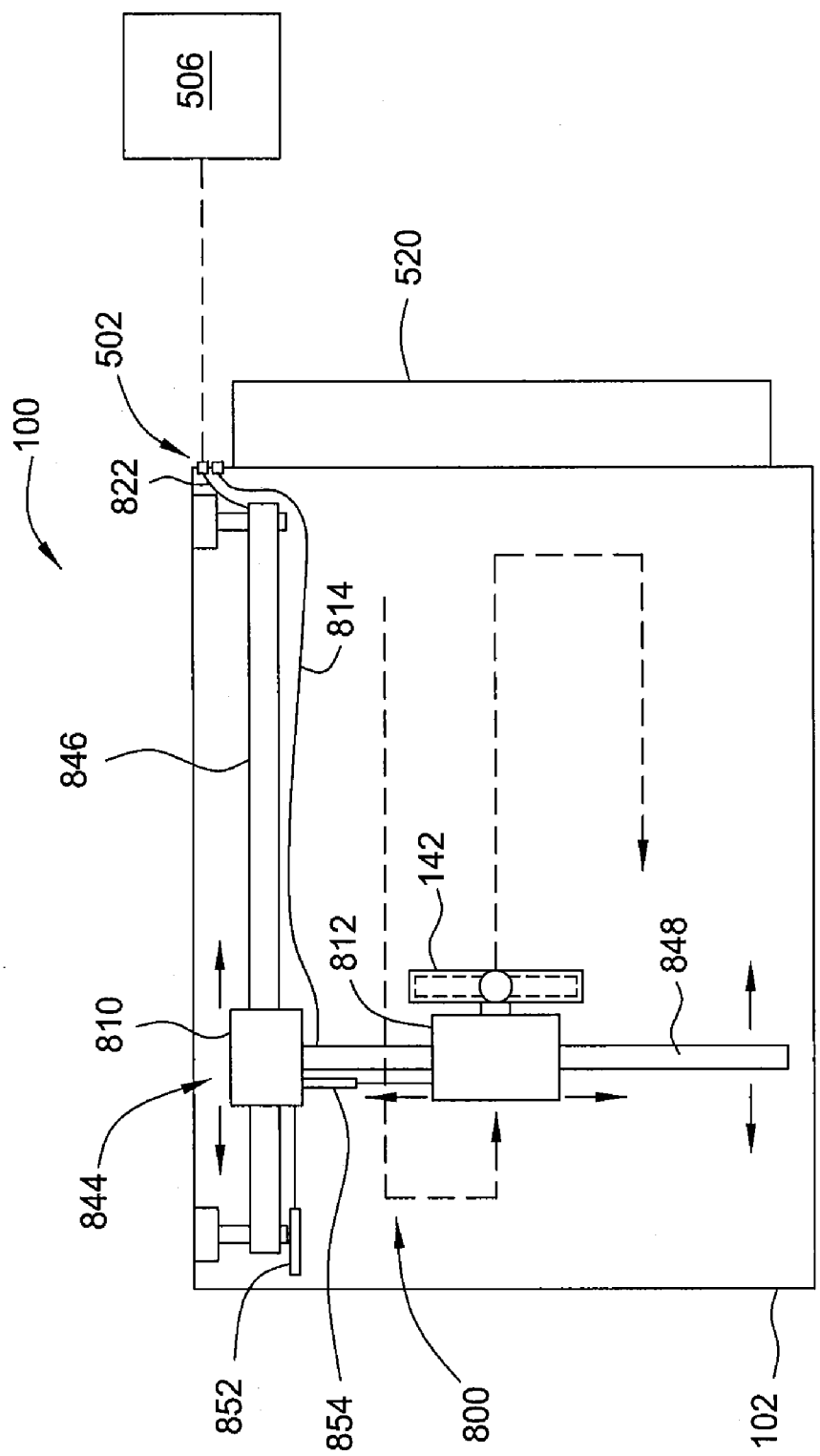
FIG. 8 depicts one embodiment of an autoscan mechanism that may be utilized in a containment system.

FIGS. 5-6 are sectional and partial sectional views of the contamination system of FIG. 2. Referring primarily to FIG. 5, an autoscan mechanism 130 may be disposed in the housing 102 to facilitate scanning of the filter 104 without opening the housing 102. Since this area of the housing 102 no long requires door to facilitate testing (such as the conventional system of FIG. 1), the length of the housing 102 may be further reduced. Moreover, as no door is required, another potential leak point present in conventional systems is eliminated, further increasing the safety factor of the present invention. In one embodiment, the total length of the housing 102 configured for autoscanning is less than about 55 inches. It is contemplated that air from a containment system configured for efficiency testing may be sampled downstream of the housing 102, thus, allowing the distance between the downstream damper 118 and filter 104 to be further shortened. One autoscan mechanism that may be adapted to benefit from the invention is described in U.S. Pat. No. 7,658,787 issued on Feb. 9, 2010 to Morse et al., which is hereby incorporated by reference in its entirety.

The autoscan mechanism 130 includes at least one probe 142 and motion mechanism, such as an actuator 144. The probe 142 may have any number of designs suitable for particulate scan testing. In one embodiment, the probe 142 conforms to IEST-RP-CC034.1 Recommended Practices. The probe 142 is generally coupled by a tube 516 coupled to a downstream sample port 508 defined through the housing 102. A tester 510, such as a photometer or particle counter, is coupled to the port 508. The tester 510 may also be coupled to the upstream sample port 540. The probe 142 is generally configured to produce isokinetic sampling at a predefined filter test velocity. It is contemplated that multiple probes, or a probe having multiple sampling ports (and hence, multiple sampling tubes 516 coupled to multiple sampling ports 508) may be utilized.

The actuator 144 may be one or more linear actuators, x/y actuators or other mechanisms suitable for positioning the probe 142 relative to the filter element 104 thereby facilitating leak testing. Controls and/or utilities for the actuator 144 may be routed through ports 502 defined through the housing 102 to a controller 506. The ports 502 are configured to prevent leakage from the housing 102, and may be fitted with a quick-disconnect or other suitable fitting. Such ports are currently available on containment systems available from Camfil Farr, Inc.

FIG. 8 depicts one embodiment of an autoscan mechanism 800 that may be used in the housing 102 described herein to leak test a filter installed in the system 100 without opening the housing 102. The autoscan mechanism 800 includes a motion mechanism 844 utilized to position the probe 142 within the housing such that the entire face of the filter may be scanned for leaks. The probe 142 may be positionable to leak test the filter-to-sealing face seal for leaks as well. The motion mechanism 844 may be one or more of any suitable actuator, robot, x-y actuator, a linear actuator, a stepper or servo motor, a fluid power cylinder, a rod-less cylinder, a chain or belt drive, a rack and pinion gear arrangement, a ball, lead, acme or other power screw, or other suitable motion control, motion generating and/or motion facilitating mechanism suitable for moving the probe 142 within the interior volume of the housing 102. In the embodiment depicted in FIG. 8, the motion mechanism 844 is two rod-less cylinders 846, 848.

The first cylinder 846 is coupled to the housing 102 and has a first carriage 810 slideably coupled thereto. The second cylinder 848 is coupled to and moves with the first carriage 810. The second carriage 812 rides along the second cylinder 848. The probe 142 is coupled to the second carriage 812. The position of the first carriage 810 is controlled by selectively applying air or other fluid to at least one side of the first cylinder 846. Likewise, the position of the second carriage 812 is controlled by selectively applying air or other fluid to at least one side of the second cylinder 848. Thus, by controlling the motion of the carriages 810, 812, the probe 142 may be selectively positioned to scan the face of the filter. In the embodiment shown, fluid control lines 822, 824 are provided between the cylinders 846, 848 and ports 502 to control the lateral position of the probe 142 in the scan direction from outside of the system 100.

Sensors disposed in the system 100 may be utilized to provide to the feedback controller for determining the position of the probe 142. This information may be utilized to confirm leaks, or to test filter leak repairs, among other uses. In the embodiment depicted in FIG. 8, two sensors 852, 854, are wired to a controller 506 through the ports 502 to provide information that may be utilized to determine when the probe 142 is in a predefined position. The wiring between the sensors 852, 854 and the controller 506 has been omitted for the sake of clarity. The sensors 852, 854 may be utilized in calibration routines, or to calculate the probe position utilizing a known or calculated rate of probe travel. The probe travel rate may be determined empirically, calculated based on known or estimated rates associated with control fluid parameters (i.e., pressure, volume and/or rate of fluid passing through control lines 848, 850) and/or by direct measurement.

In another embodiment, the sensors 852, 854 are disposed in the housing 102 to obtain a metric indicative of probe position. The sensors 852, 854 may be an optical device, a proximity sensor, a rotary encoder, a linear variable differential transformer (LVDT) transducer or other device suitable for determining the position of the probe 142. In the embodiment depicted in FIG. 8, the sensor 852, 854 are LVDT transducers wired to the controller 506 through the ports 502.

Returning to FIGS. 2 and 5, the housing 102 generally includes a door 520 that may be utilized to sealingly close a filter access port 522. The door 520 generally includes a gasket 524 that may be compressed against the housing 102 to seal the port 522. In one embodiment, the gasket 524 is compressed by a locking mechanism 526, such as a knob disposed on a threaded member. As the housing 102 only requires a single door or access port for accessing the interior of the housing 102 (e.g., solely the filter access port 522), the number of potential leak points are minimized to solely the single door, the housing edge welds, and the penetrations, thus providing a more robust and reliable containment system as compared to conventional systems. As the critical nature of the hazard level associated with the use of containment systems continues to increase, containment systems, such as the invention described herein having minimized leak potential, will become a necessity for protecting technicians and the areas surrounding the labs utilizing these systems.

Continuing to refer to FIGS. 2 and 5, a bag ring 530 circumscribes the filter access port 522. The ring 530 provides a mounting flange for a bag (optionally with gloves) 532 may be utilized to remove and/or access the interior of the housing 102 as know in the art. This method for accessing the interior of the housing is generally known as "bag-in, bag-out", and is described in further detail in U.S. Pat. No. 4,450,964, which is incorporated by reference in its entirety.

The filter 104 is generally sealed against a sealing face 550 disposed in the housing 102. The sealing face 550 is coupled to the housing 102 in a manner that forces air, flowing through the housing, to pass through the filter 104. In one embodiment, the sealing face 550 is a knife edge for engaging a fluid seal formed in a frame of the filter 104. It is contemplated that the sealing face 550 may be a flange for seating a gasket, among other configurations suitable for sealing the filter 104 to the housing 102.

The housing 102 also includes a biasing mechanism 552. The biasing mechanism 552 generally urges the filter 104 against the sealing face 550 to ensure no by-passage during operation. In one embodiment, the biasing mechanism 552 is a linkage clamping mechanism which may be moved between a position that releases the filter 104, and a position that biases the filter against the sealing face 550. It is contemplated that other configurations of a biasing mechanism 552 may be utilized that are suitable for holding the filter 104 against the sealing face 550. One contamination housing that may be adapted to benefit from the invention having both a biasing mechanism, bag ring and filter access port is a FB HOUSING™, available from Camfil Farr, Inc., located in Washington, N.C.

Figure 7:
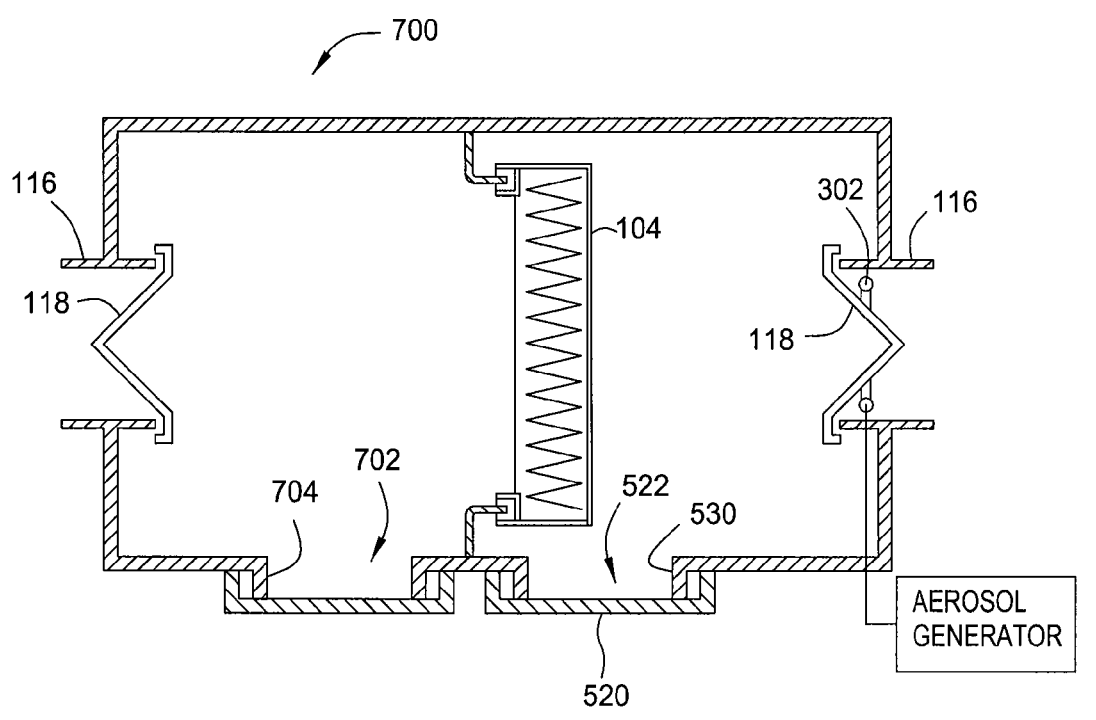

FIG. 7 depicts another embodiment of a containment system 700 having integrated dampers 118. The containment system 700 is generally similar to the system of FIGS. 2-6, except wherein the system 700 includes a second access port 702 with bag ring 704 to accommodate manual testing of the filter 104 utilizing conventional scanning practices using a bag with gloves, such as the bag 532 shown in FIG. 5.

Thus, a containment system having at least one integrated damper is provided that has a substantial reduction in overall size and cost compared to conventional containment systems. Moreover, embodiments having an autoscan mechanism that enable testing of a filter in its installed location (e.g., operational location at the final users site, not bench testing) without opening the housing and exposing the area downstream of the filter to the risk of contamination.

What is claimed is:

1. A method for replacing a filter disposed in a containment housing, comprising:
    moving a first damper disposed in a housing to a closed position that provides an air-tight seal of an inlet of the housing;
    moving a second damper disposed in the housing to a closed position that provides an air-tight seal of an outlet of the housing;
    opening an access door having a bagging ring coupled to the housing;
    installing a replacement filter in the housing;
    testing the replacement filter disposed in the housing;
    moving the first damper and the second damper to an open position that allows air flow through the containment housing and the replacement filter tested in the housing.

2. The method of claim 1, further comprising
    performing an bag-in/bag-out filter exchange through the access door.

3. The method of claim 1, wherein the testing the replacement filter is performed at a location downstream of the containment housing.

4. The method of claim 1, wherein the testing the replacement filter comprises:
    introducing an aerosol challenge into air flowing into the housing in a radially inward direction.

5. The method of claim 1, wherein the testing the replacement filter comprises introducing an aerosol challenge into air flowing into the housing at a location upstream of the first damper.

6. The method of claim 1, wherein the testing the replacement filter comprises scanning the replacement filter disposed in the housing without opening the housing.

7. The method of claim 6, wherein scanning further comprises scanning the replacement filter with a scan probe having a plurality of sampling ports.

8. The method of claim 1, wherein the testing the replacement filter comprises performing an efficiency test.

9. The method of claim 1, wherein the testing the replacement filter comprises testing the filter-to-sealing face seal.

10. The method of claim 1, wherein the testing the replacement filter comprises determining a leak in the replacement filter.

11. The method of claim 1, wherein the testing the replacement filter comprises determining a position of a leak in the replacement filter.

* * * * *